US012773167B2

(12) United States Patent
Kwon et al.

(10) Patent No.: US 12,773,167 B2
(45) Date of Patent: Oct. 27, 2026

(54) POLYMER ENCLOSURE WITH WIRE PASSTHROUGH FOR IMPLANTABLE DEVICE

(71) Applicant: Neuralink Corp., Fremont, CA (US)

(72) Inventors: Ik Soo Kwon, San Francisco, CA (US); Dongjin Seo, San Francisco, CA (US); John W.F. To, Castro Valley, CA (US)

(73) Assignee: Neuralink Corp., Fremont, CA (US)

( * ) Notice: Subject to any disclaimer, the term of this patent is extended or adjusted under 35 U.S.C. 154(b) by 1296 days.

(21) Appl. No.: 17/529,224

(22) Filed: Nov. 17, 2021

(65) Prior Publication Data

US 2023/0148968 A1 May 18, 2023

(51) Int. Cl.

| | |
|---|---|
| ***A61B 5/00*** | (2006.01) |
| ***A61B 5/293*** | (2021.01) |
| ***A61N 1/375*** | (2006.01) |
| ***H01B 3/30*** | (2006.01) |
| ***H01B 7/04*** | (2006.01) |
| ***H01B 13/22*** | (2006.01) |
| *G06F 3/01* | (2006.01) |

(52) U.S. Cl.

CPC ............ *A61B 5/6868* (2013.01); *A61B 5/293* (2021.01); *A61N 1/3754* (2013.01); *H01B 3/306* (2013.01); *H01B 7/048* (2013.01); *H01B 13/22* (2013.01); *A61B 2562/0209* (2013.01); *A61B 2562/125* (2013.01); *G06F 3/015* (2013.01)

(58) Field of Classification Search

CPC ............................ A61B 5/6868; A61N 1/3754

See application file for complete search history.

(56) References Cited

U.S. PATENT DOCUMENTS

| | | | | |
|---|---|---|---|---|
| 4,179,319 | A * | 12/1979 | Lofdahl .................. | B32B 27/08 428/137 |
| 11,107,703 | B2 | 8/2021 | Tolosa et al. | |
| 11,444,056 | B2 | 9/2022 | Chen et al. | |
| 2014/0345934 | A1 * | 11/2014 | Markham ................ | H02G 3/22 174/650 |
| 2017/0232250 | A1 * | 8/2017 | Kim ..................... | A61N 1/0543 607/116 |
| 2018/0296243 | A1 | 10/2018 | Hanson et al. | |
| 2020/0086111 | A1 | 3/2020 | Young et al. | |

* cited by examiner

*Primary Examiner* — Livius R. Cazan

(74) *Attorney, Agent, or Firm* — Oblon, McClelland, Maier & Neustadt, L.L.P.

(57) ABSTRACT

An implantable device and method of manufacture include a substantially hermetic polychlorotrifluoroethylene (PCTFE) enclosure with closely-spaced wires extending through a slit in the enclosure. A method for manufacturing the implantable device includes cutting a slit in a piece of polymer and extending a plurality of insulated wires through the slit. Each of the insulated wires are parallel to a neighboring wire of the insulated wires. The piece of polymer is thermally bonded around each wire of the plurality of insulated wires such that the piece of polymer is sealed around insulation of each wire with a portion of each wire extending through the piece of polymer.

14 Claims, 12 Drawing Sheets

700

800

POLYMER ENCLOSURE WITH WIRE PASSTHROUGH FOR IMPLANTABLE DEVICE

CROSS-REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Implantable devices are used for a variety of applications such as cardiac pacemakers, cochlear implants, and recording and stimulating electrical signals in target biological tissue. In many cases, active electronic devices are critical to the functionality of the implantable device. Body environments such as brain tissue, heart tissue, and the like have high humidity and bodily fluids. Implantable devices are generally in an in-vivo environment including high humidity and oxidative inflammatory response that will put stress on sensitive components such as active electronics without proper protection. As a result, implantable devices generally have a rigid hermetic housing to protect the active electronics from environmental and mechanical stress. Such housings are commonly manufactured from glass or metal, which are suitable for a variety of applications due to the hermetic nature of these materials.

As implantable devices advance, it is increasingly common to have a large number of wires extending from the implantable device. For example, a brain-machine interface includes as many as thousands of wires extending from an implantable device and implanted in a brain. In such applications, with a large number of tightly spaced wires extending through the housing, problems arise that make traditional housing materials less suitable for these applications. For example, a glass housing can crack or otherwise fail if manufactured with tightly spaced wires extending through the glass.

BRIEF SUMMARY OF THE INVENTION

In some embodiments, a method for manufacturing an implantable device includes cutting a slit in a piece of polymer; extending a plurality of insulated wires through the slit, each wire of the insulated wires being parallel to a neighboring wire of the insulated wires; and thermally bonding the piece of polymer around each wire of the plurality of insulated wires such that the piece of polymer is sealed around insulation of each wire with a portion of each wire of the plurality of insulated wires extending through the piece of polymer.

In some aspects, insulation of the insulated wires is composed of polyimide. In some aspects, the polymer comprises polychlorotrifluoroethylene (PCTFE). In some aspects, before the thermally bonding, the method further includes placing the piece of polymer, with the plurality of insulated wires disposed through the slit, into a mold. In some aspects, the thermally bonding comprises applying pressure to the piece of polymer and the plurality of insulated wires in the mold and heating the piece of polymer and the plurality of insulated wires.

In some aspects, the piece of polymer and the insulated wires are heated to a temperature between 250 degrees Celsius (C) and 350 degrees Celsius (C). In some aspects, the thermally bonding is performed for between 10 minutes and 15 minutes. In some aspects, the thermally bonding is performed in a pure nitrogen environment. In some aspects, the extending the plurality of insulated wires through the slit is performed at less than 100 degrees Celsius (C).

In some aspects, the method further includes, before the thermally sealing, placing the piece of polymer, with the plurality of insulated wires disposed through the slit, into a mold, wherein the mold comprises an opening; and when the piece of polymer, with the plurality of insulated wires disposed through the slit, is placed in the mold, a plurality of probes extend flatly through the opening in the mold. In some aspects, the method further includes, before the thermally bonding, disposing a stiffener onto the plurality of insulated wires. In some aspects, the stiffener is composed of poly (4,4'-oxydiphenylene-pyromellitimide). In some aspects, the piece of polymer is a first piece of polymer, and the method further includes obtaining a second piece of polymer; and after the thermally bonding, thermally sealing the first piece of polymer to the second piece of polymer.

In some embodiments, an implantable device includes an enclosure composed of polychlorotrifluoroethylene (PCTFE); a seam disposed on a surface of the enclosure; and a plurality of insulated wires, each wire of the plurality of insulated wires separated by less than 100 micrometers (μm) from a neighboring wire of the plurality of insulated wires, the plurality of insulated wires extending through the seam perpendicular to the surface of the enclosure such that the enclosure is sealed around the plurality of probes.

In some aspects, insulation of the insulated wires is composed of polyimide (PI). In some aspects, the plurality of insulated wires comprises at least 500 insulated wires. In some aspects, each insulated wire, of the plurality of insulated wires, includes a plurality of metal traces terminating in respective electrodes. In some aspects, the electrodes are implanted in a brain. In some aspects, the enclosure is sealed substantially hermetically. In some aspects, the implantable further includes an opening in the enclosure; and one or more of: an integrated circuit, a wireless communication device, or a wireless charging device sealed within the opening.

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

DETAILED DESCRIPTION OF THE INVENTION

Figure 1:
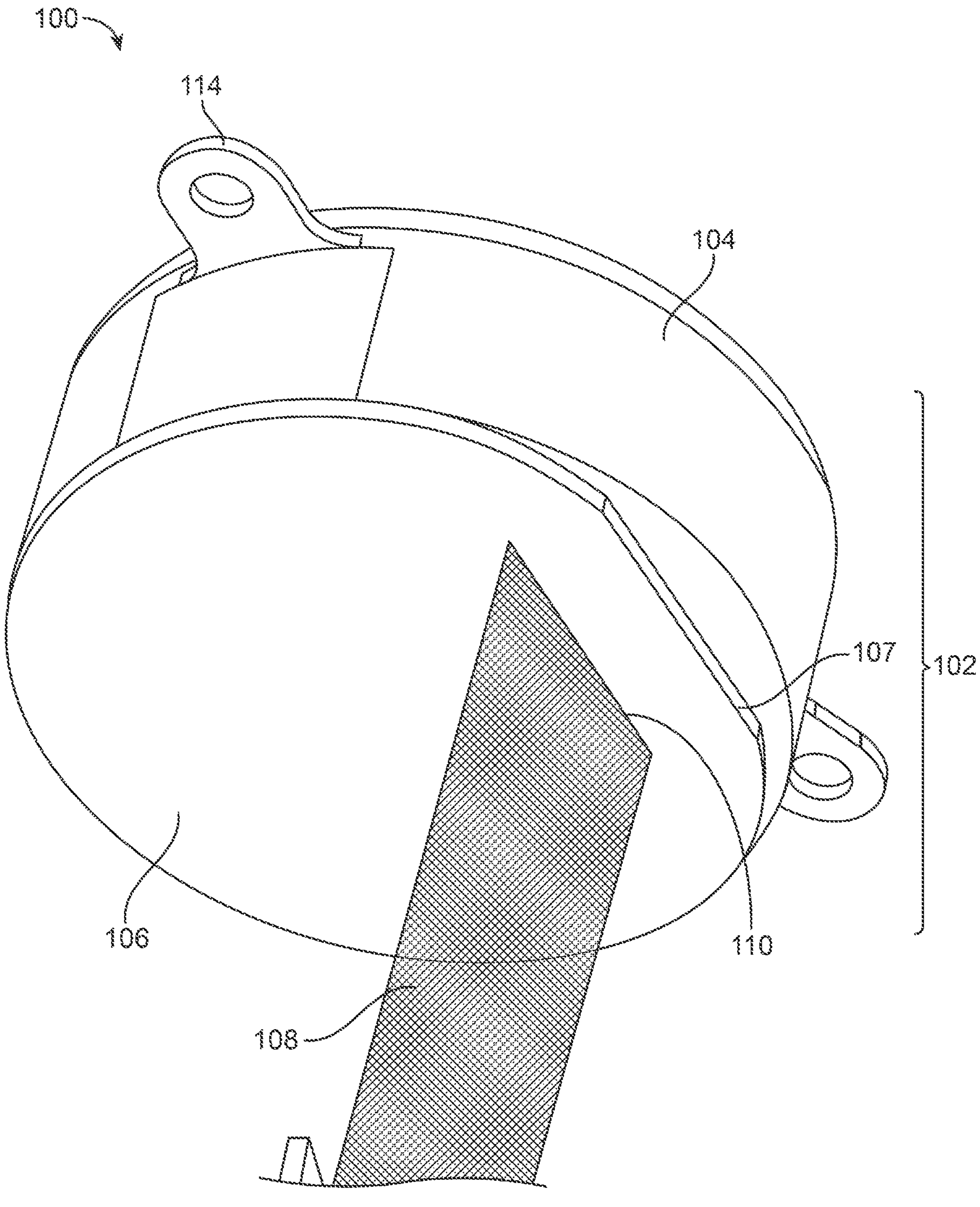
FIG. 1 illustrates an implantable device with a polymer enclosure with bottom passthrough slit, according to an aspect of the present disclosure.

The present disclosure relates to systems and methods of manufacturing an implantable device with a polymer enclosure with a passthrough slit. Polymers such as PCTFE can be sealed substantially hermetically around wires insulated with certain polymers, even when the wires are densely packed together. For example, a PCTFE enclosure can provide a substantially hermetic seal while being bonded around hundreds or thousands of insulated wires spaced apart closely, on the order of micrometers (μm). By extending these wires through a passthrough slit on a bottom surface of the enclosure, the wires can extend straight down from the passthrough slit for implantation. This configuration prevents bending or straining the wires. The use of a feedthrough slit also allows for the use of relatively high temperature and pressure in the manufacturing process which can further help ensure a substantially hermetic seal.

As noted above, conventional enclosure materials suffer from several limitations. Implantable devices are traditionally enclosed using materials such as glass, titanium, or ceramic. These materials are generally well-suited as they fit the bill for creating a hermetic or substantially hermetic environment within the enclosure, as well as being biocompatible (e.g., not cytotoxic). However, as implantable devices evolve, so do the needs for the enclosure. In particular, devices are increasingly developed with large numbers of electrodes extending from the enclosure into tissue. For example, a brain-machine interface (BMI) uses multiple electrodes to stimulate brain tissue and record neurological signals. BMIs have the potential to help people with a wide range of clinical disorders, and have been applied in contexts such as neuroprosthetic control of computer cursors, robotic limbs, and speech synthesizers. Development of BMIs has been limited historically by an inability to record from large numbers of neurons. Due to recent developments in electrode fabrication, robotic insertion, electronic design, and signal processing, there is now the ability to implant a BMI with thousands of electrodes. This new generation of BMIs can include thousands of wires spaced relatively closely together (e.g., micron-level spacing) and connected to sensitive electronics. However, this means that traditional enclosure approaches are no longer feasible. Rigid materials such as glass may crack when manufactured with tightly-spaced openings to accommodate thousands of channels.

Techniques described herein address these issues. An enclosure is composed of a polymer such as PCTFE. A set of wires are insulated with a polymer such as PI. The wires extend through the enclosure via a passthrough slit. To manufacture the enclosure, a reflow process is used to bond the PI insulation to the PCTFE to form a substantially hermetic seal around the wires. The position of the slit is leveraged so that the wires extend straight through the enclosure perpendicular to the surface of the enclosure.

Many of the details, dimensions, angles and other features shown in the Figures are merely illustrative of particular embodiments. Accordingly, other embodiments can include other details, dimensions, angles and features without departing from the spirit or scope of the present invention. Various embodiments of the present technology can also include structures other than those shown in the Figures and are expressly not limited to the structures shown in the Figures. Moreover, the various elements and features shown in the Figures may not be drawn to scale. In the Figures, identical reference numbers identify identical or at least generally similar elements.

As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as shown in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below, depending on the context of its use. The device may be otherwise oriented (rotated 90 degrees or at other orientations) and the spatially relative descriptors used herein are interpreted accordingly.

Although the terms "first", "second", etc. may be used herein to describe various elements, components, regions, layers and/or sections, it should be understood that they should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As used herein, the terms "and/or" and "at least one of" include any and all combinations of one or more of the associated listed items.

As used herein, the terms "approximately" and "about" are used to provide flexibility to a numerical range endpoint by providing that a given value may be within a functional range greater than or less than the given value. As used herein, unless otherwise specified, the given value modified by approximately or about is modified by ±10%.

Device with PCTFE Enclosure with Passthrough Slit

FIG. 1 illustrates an implantable device 100 according to some embodiments. The implantable device 100 includes an enclosure 102. The enclosure 102 includes a first piece of polymer 106 and a second piece of polymer 104. Multiple insulated wires 108 extend out of the enclosure 102.

As shown in FIG. 1, the first piece of polymer 106 and the second piece of polymer 104 are joined together to form the enclosure 102. The first piece of polymer 106 may be a bottom portion, and the second piece of polymer 104 may be a top portion. The first piece of polymer may include one or more flat surfaces. The shape of the first piece of polymer 106 may be substantially circular, as is shown in FIG. 1. In some implementations, one edge 107 of the first piece of polymer is flattened off so that the first piece of polymer 106 is semicircular, as shown in FIG. 1. In other implementations, the first piece of polymer 106 may have other suitable shapes, such as square, rectangular, triangular, etc.

In some embodiments, the first piece of polymer 106 and the second piece of polymer 104 are composed of polychlorotrifluoroethylene (PCTFE). PCTFE is a polymer, specifically, a thermoplastic chloro-fluoropolymer with the molecular formula $(CF_2—CFCl)_n$, where n is the number of monomer units in the polymer molecule. PCTFE is similar to polytetrafluoroethylene (PTFE), except that PCTFE is a homopolymer of the monomer chlorotrifluoroethylene (CTFE) instead of tetrafluoroethene. PCTFE is manufactured and sold under trade names including Kel-F®, FluoroPro™, Neoflon®, and Aclar®. CTFE has similar properties to PCTFE and may be used as the enclosure 102 material alternatively or additionally.

In some embodiments, the implantable device 100 may include a volume holding circuitry, which can have variable shapes and sizes, and can be configured to remain in vivo within a subject following surgery. The implantable device can be, for example, disposed within a skull. The implantable device can further include a communications relay to transmit and receive signals to and from the implantable device. In some aspects, the implantable device can further include a wireless communications port, including an antenna configured to transmit radio frequencies, Wi-Fi frequencies, or the like, in order to relay data, electricity (e.g. for charging the probe device), or other signals.

Active electronic devices are critical components to the functionality of implantable medical devices, as without the electronic components, an active implantable medical device would not be able to perform as designed. The enclosure should be substantially hermetic to protect the active electronics from contacting the body environment, which can have high moisture, humidity, and oxidative properties. A hermetic enclosure will completely prevent the passage of liquids or gases. A substantially hermetic enclosure will prevent the passage of liquids or gases for a time on the order of years. For example, certain polymers may allow a small amount of gas or liquid to pass through after tens of years, which would be considered substantially hermetic.

PCTFE has several properties that are desirable for use in an implantable device. The physical properties and chemical properties of PCTFE allow it to be stable to withstand the harsh environment in-vivo, including high humidity and oxidative inflammatory biological response. PCTFE has good chemical resistance. Due to its high fluorine content and lack of hydrogen atoms, PCTFE is resistant to the attack by most chemicals and oxidizing agents. PCTFE also provides the rigidity needed to prevent mechanical stress on the implantable device, particularly on active electronics enclosed by the enclosure. Furthermore, PCTFE has a low dielectric constant that allows Bluetooth Low Energy (BLE) communication and makes wireless charging possible.

Another advantageous aspect about PCTFE is its barrier properties. PCTFE is substantially hermetic. PCTFE has a close to zero water absorption value of <0.01% (ISO 62). PCTFE also processes low water vapor permeability. PCTFE is a fluororesin with the highest gas barrier property with a WVTR (0.005 g/m2/24 hr) at 25° C. These properties are ideal for development of a substantially hermetic package.

PCTFE also processes several desirable mechanical properties and thermal properties. PCTFE has high tensile strength (ASTM D1708: 47 MPa), and moderate hardness (ASTM D638 Shore D 80). PCTFE has a melting point of 212° C. and a maximum temperature for continuous use of 120° C.). PCTFE also has glass transition temperature of 45° C. and good melt flow properties with excellent stress crack resistance. These properties make PCTFE suitable for compression molding, injection molding, precision molding and machining into desired shapes and parts and are ideal for a thermocompression bonding process. The mass flow properties of PCTFE allow it to reflow and fuse with itself at temperature above its melting point. The sealing steps described herein allow the first and second portions of the PCTFE enclosure to fuse around insulated wires following a thermocompression bonding.

In some implementations, the first piece of polymer 106 and/or the second piece of polymer 104 includes one or more attachment means 114 to attach the implantable device 100 to a subject for implantation. In the example shown in FIG. 1, the attachment means 114 are in the form of screw holes for attaching the implantable device 100 to a subject. For example, the implantable device can be disposed on a skull of a subject, and screws can be inserted through the attachment means 114 to hold the implantable device 100 in place near the skull of the subject.

A slit 110 is disposed in the first piece of polymer 106. The slit 110 is an opening in the first piece of polymer 106 sized so that the insulated wires 108 fit through the slit. In some implementations, the slit 110 extends across the first piece of polymer 106 partially, without extending to the edges, as shown in FIG. 1.

The insulated wires 108 pass through the slit 110 so that they extend straight down and are perpendicular to the bottom surface of the enclosure 102. The first piece of polymer 106 is sealed around the insulated wires 108. In some embodiments, the plurality of insulated wires 108 includes at least 500 wires. In some embodiments, more than 1,000 wires 108 extend through the slit 110. In some implementations, each of the insulated wires 108 are parallel to each other.

In some embodiments, the wires 108 are spaced apart by a distance on the on the order of micrometers (μm). Each wire may be separated by less than 100 micrometers (μm) from a neighboring wire. For example, the wires are spaced apart by 50 μm, 40 μm, 30 μm, 25 μm, or 20 μm. In some embodiments, each wire is separated by between 10 micrometers (μm) and 50 micrometers (μm) from a neighboring wire.

In some embodiments, disposed within each of the insulated wires 108 is a set of metal traces. The metal traces are individual metallic threads within the insulation (e.g., each insulated wire 108 is made up of insulation surrounding multiple long metallic strands). In some implementations, each of the insulated wires 108 includes 16 metal traces. Alternatively, the insulated wires 108 can include any suitable number of metal traces, such as 2, 4, 5, 6, 8, 12, or 32 metal traces. In some embodiments, each of the metal traces is about 2 micrometers (μm) from a neighboring metal trace. The metal traces may be about 2 micrometers (μm) in cross sectional width.

In some embodiments, each of the metal traces terminates in an electrode. The metal traces may have one end within the implantable device 100 and another end with an electrode. The electrode may be configured to send and/or receive signals to/from tissue, such as brain tissue. In some embodiments, the electrode is implanted in a brain. In some implementations, the insulated wires are in the form of a polyimide (PI) thin film electrode array. The a polyimide film is microfabricated to have embedded wire traces and electrodes at the distal end.

Within the enclosure, in some implementations, the metal traces are connected to circuitry (not visible). For example, the implantable device includes a volume disposed between the first portion of the enclosure and the second portion of the enclosure. Sealed within the volume is circuitry which may include one or more integrated circuits. The implantable device may further include, sealed within the volume of the enclosure, communications components such as a wireless communication device, and power components such as a wireless charging device. An example of an implantable device with such components is illustrated and described in further detail in U.S. patent application Ser. No. 16/926,420, "Brain Implant with Subcutaneous Wireless Relay and External Wearable Communication and Power Device," which is incorporated by reference herein in its entirety.

Figure 2:
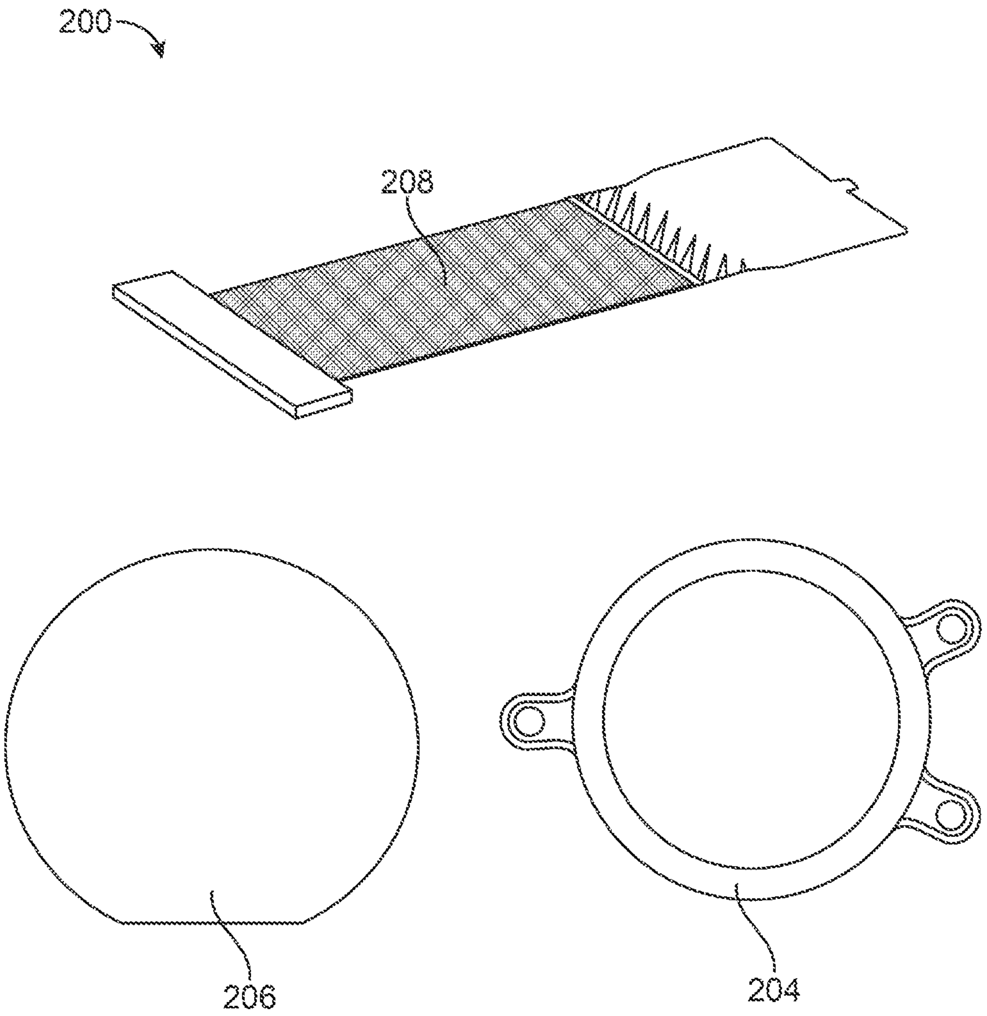
FIG. 2 illustrates components of an enclosure, according to an aspect of the present disclosure.

FIG. 2 illustrates components of an enclosure, according to an aspect of the present disclosure. The enclosure includes insulated wires 208, a first piece of polymer 206, and a second piece of polymer 204. The pieces of polymer 204 and 206 are configured to form an enclosure when assembled together, as described above with respect to FIG. 1. The insulated wires 208 can extend out of the enclosure, e.g., through a slit in one of the pieces of polymer, as described above with respect to FIG. 1.

Manufacturing a Polymer Enclosure with Passthrough Slit

Figure 3A:
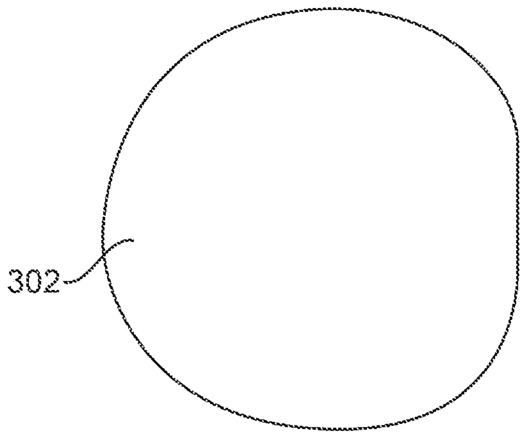
FIG. 3A illustrates a piece of polymer before slit fabrication, according to an aspect of the present disclosure.

FIG. 3A illustrates a piece of polymer 302 before slit fabrication, according to an aspect of the present disclosure. In some embodiments, the piece of polymer 302 may form the bottom of an enclosure such as that shown in FIG. 1 when joined with another piece of polymer. The piece of polymer 302 includes a flat surface and is composed of a substantially hermetic polymeric material such as PCTFE.

Figure 3B:
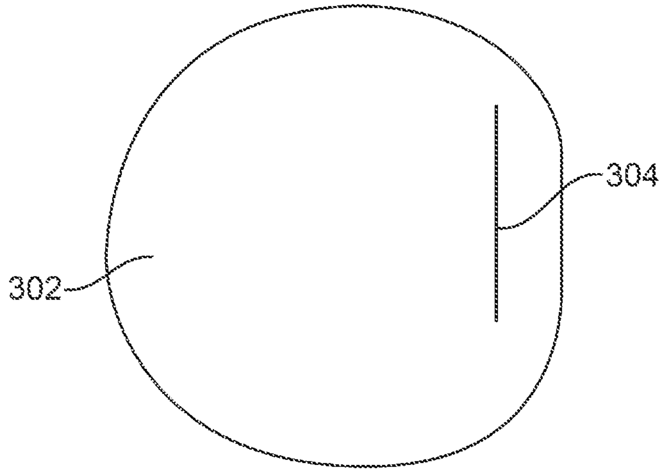
FIG. 3B illustrates a piece of polymer during slit fabrication, according to an aspect of the present disclosure.

FIG. 3B illustrates a piece of polymer 302 during slit fabrication, according to an aspect of the present disclosure. A slit 304 is formed in the piece of polymer 302. For example, a blade or knife can be used to cut the slit 304 in the piece of polymer 302. The slit 304 may be cut across the piece of polymer 302 partially, without extending to the edges, as shown in FIG. 3B. Alternatively, the piece of polymer 302 may be cut all the way across, so that the piece of polymer 302 is cut into separate portions.

Figure 3C:
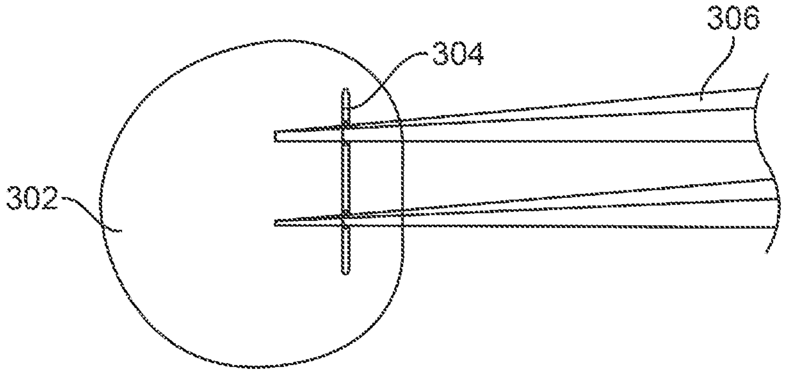
FIG. 3C illustrates a piece of polymer during slit fabrication, according to an aspect of the present disclosure.

FIG. 3C illustrates a piece of polymer 302 during slit fabrication, according to an aspect of the present disclosure. After forming the slit 304, the slit may be widened to accommodate the insulated wires. For example, forceps or tweezers 306 are placed in the slit 304, and the slit 304 is stretched or widened. The slit 304 may be sized to accommodate the insulated wires. For example, the slit 304 is slightly wider and longer, but comparable to, the cross-sectional size of a set of insulated wires. The slit 304 may then be sanded or otherwise smoothed so that insulated wires can be inserted into the slit 304 without damage to the insulated wires.

Figure 4:
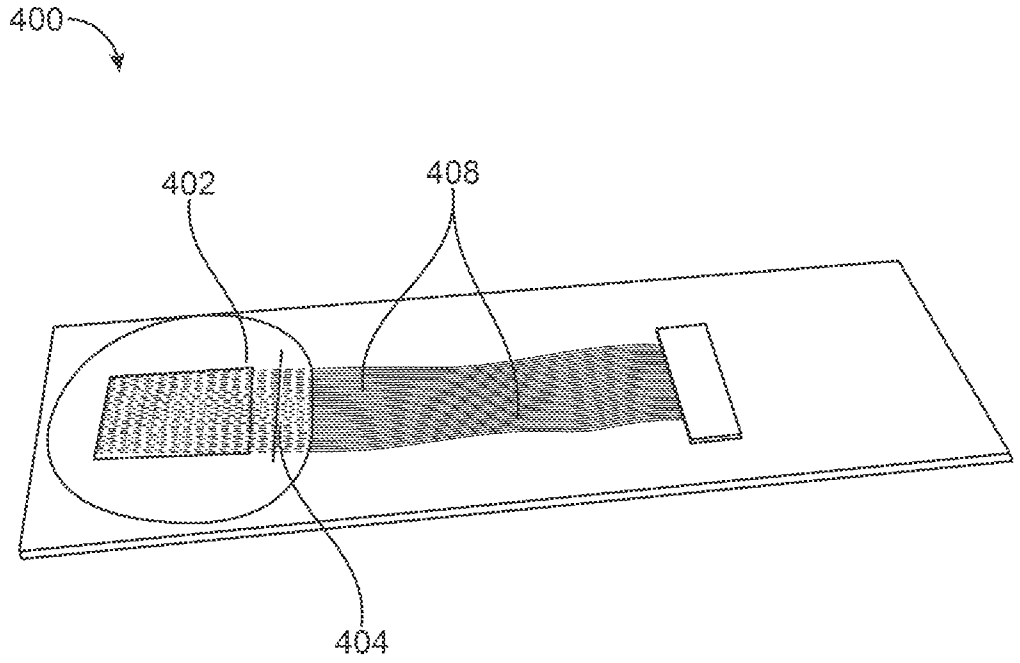
FIG. 4 illustrates a piece of polymer with insulated wires inserted in a slit, according to an aspect of the present disclosure.

FIG. 4 illustrates a piece of polymer 402 with insulated wires 408 inserted in a slit 404, according to an aspect of the present disclosure. Once the slit 404 has been formed, the wires 408 can be slid through the slit, so that the wires extend through the slit, with a portion of the wires on one side of the slit, and a portion of wires on the other side of the slit. In some aspects, the wires are passed through and annealed at a temperature less than about 100 degrees C.

Figure 5:
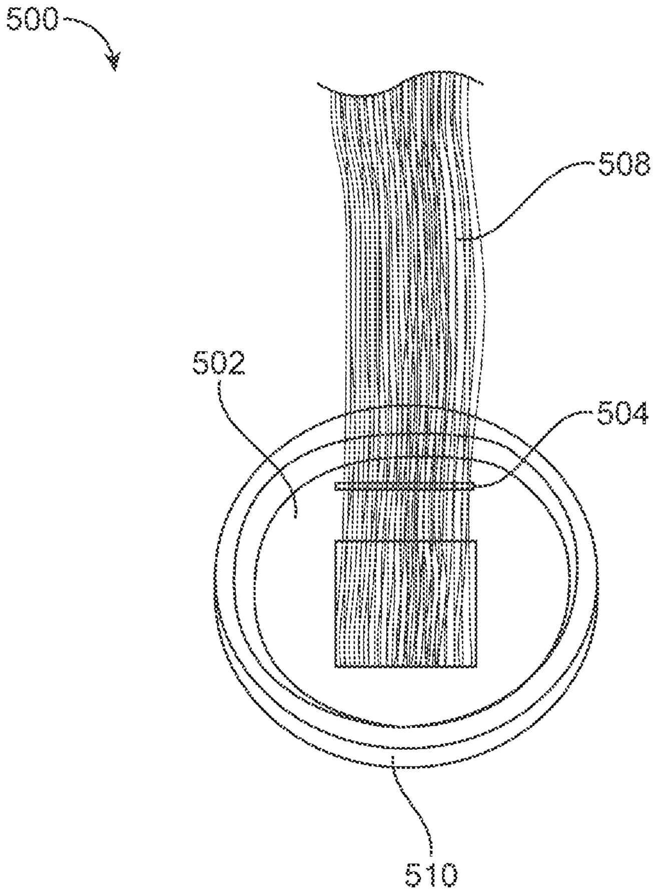
FIG. 5 illustrates a portion of an enclosure placed in a mold for sealing, according to an aspect of the present disclosure.

FIG. 5 illustrates a piece of polymer 502 placed in a mold base 510 for sealing, according to an aspect of the present disclosure. In some implementations, after inserting the insulated wires 508 through the slit 504, the piece of polymer 502, along with the insulated wires 508, are disposed in a mold base 510. The mold base 510 may be sized to tightly fit the piece of polymer 502. For example, the mold base 510 is slightly larger in diameter than the piece of polymer 502, so that the piece of polymer 502 fits snugly in the mold base 510. The piece of polymer 502 is placed in the mold base 510 so that the wires 508 extend out the top surface of the piece of polymer 502 and out of the mold base 510. As further described with respect to FIG. 11, the mold base 510 can facilitate reflow of the piece of polymer 502 to seal around each of the insulated wires 508.

Figure 6:
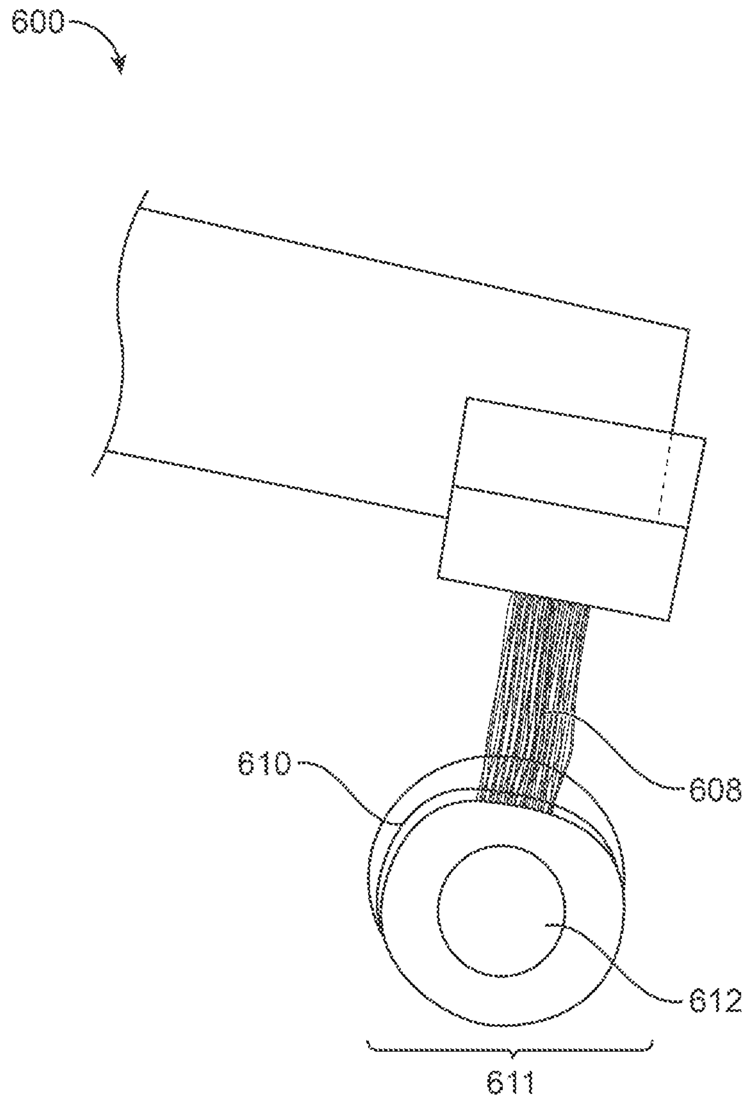
FIG. 6 illustrates a piece of polymer placed in a mold base for sealing, according to an aspect of the present disclosure.

FIG. 6 illustrates a piece of polymer placed in a mold 611 for sealing, according to an aspect of the present disclosure. As described above with respect to FIG. 5, a piece of polymer can be placed in a mold base 610. In some embodiments, the mold base 610 is part of a mold 611, along with a mold top 612. The piece of polymer (not visible in FIG. 6) may be enclosed within the mold 611 by placing the mold top 612 on top of the mold base 610 and the piece of polymer disposed in the mold base 610. The insulated wires 608 extend out of the mold 611.

In some embodiments, the mold 611 is made out of metal or any other rigid materials that do not decompose, deform, or chemically interact with the polymer at the reflow temperature and pressure applied. Depending on the need, the shape of the interior of the mold could be such that it partially or wholly follows the outline of the piece of polymer, so that when the piece of polymer is placed down in the mold 611, the mold 611 provides a fit to prevent the piece of polymer from moving around.

Figure 7:
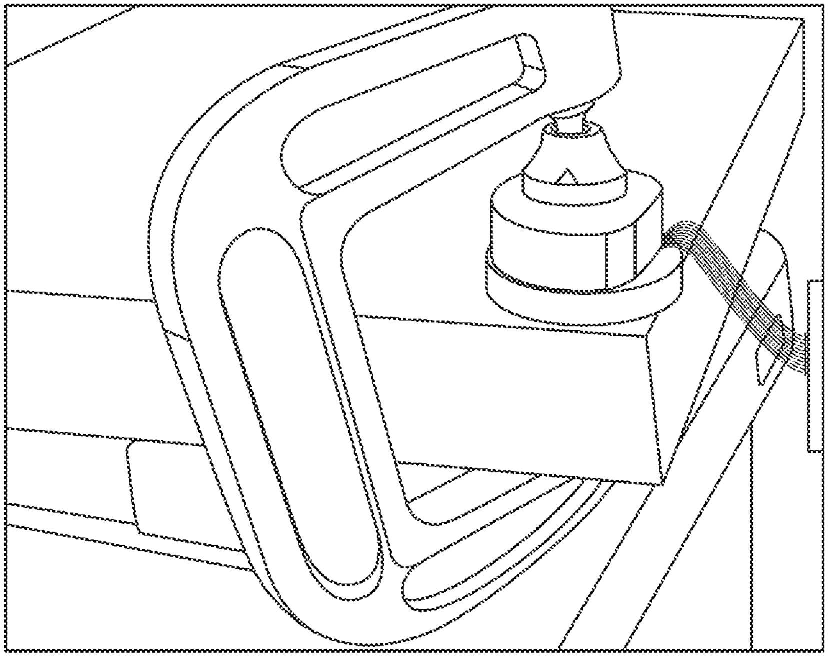
FIG. 7 illustrates a clamp for sealing a passthrough slit, according to an aspect of the present disclosure.

FIG. 7 illustrates a clamp 700 for sealing a passthrough slit, according to an aspect of the present disclosure. In some embodiments, the slit in the piece of polymer is sealed around each of the insulated wires using a thermocompression process. The clamp 700 can be a C-clamp, as shown in FIG. 7. The clamp 700 is used to apply pressure to the portion of the enclosure with the slit and insulated wires, as part of the thermocompression process.

Figure 8:
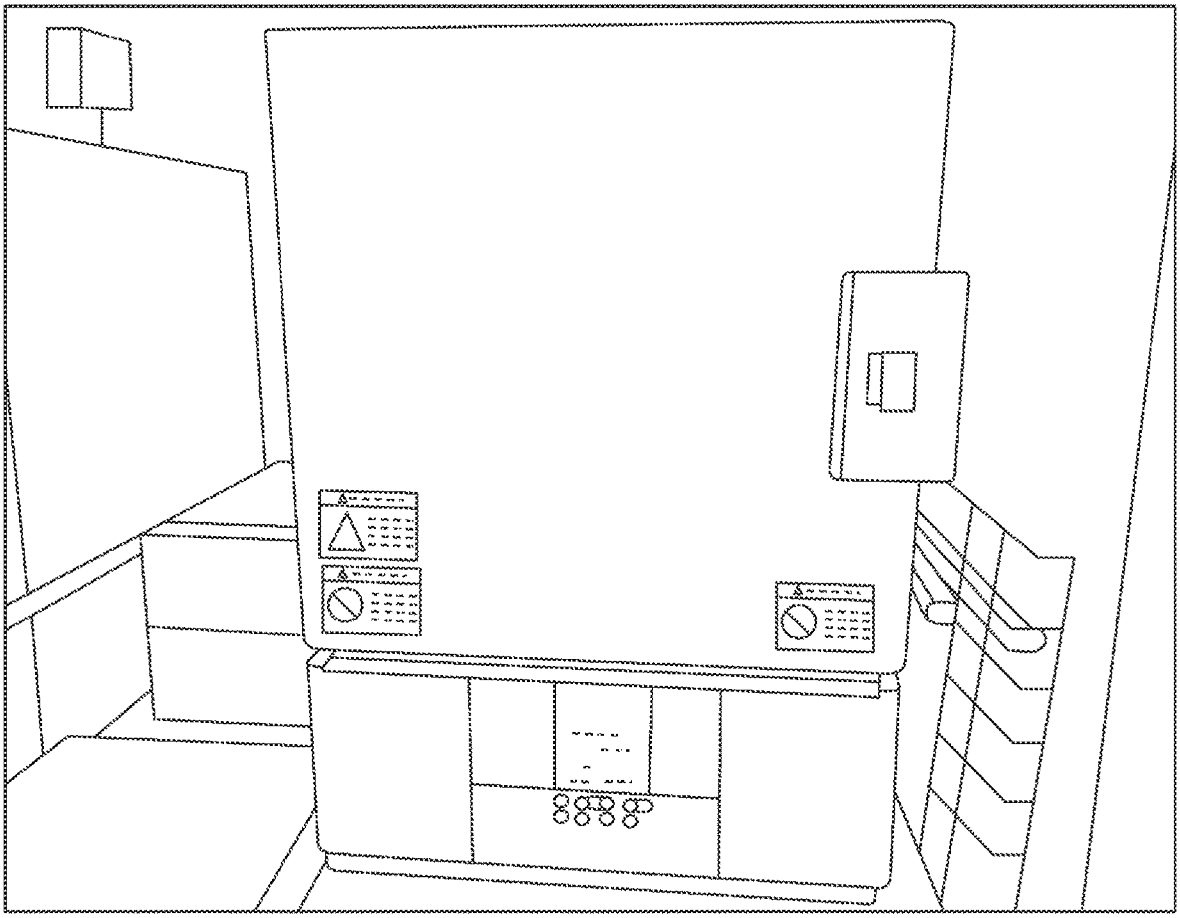
FIG. 8 illustrates a heater for sealing a passthrough slit, according to an aspect of the present disclosure.

FIG. 8 illustrates a heater 800 for sealing a passthrough slit, according to an aspect of the present disclosure. As noted above, the slit in the enclosure can be sealed around each of the insulated wires using a thermocompression process. The heater 800 can be used to apply heat to the portion of the enclosure with the slit and insulated wires, as part of the thermocompression process. The heater 800 may be a furnace capable of heating to temperatures in the range of 200-400 degrees C.

Figure 9A:
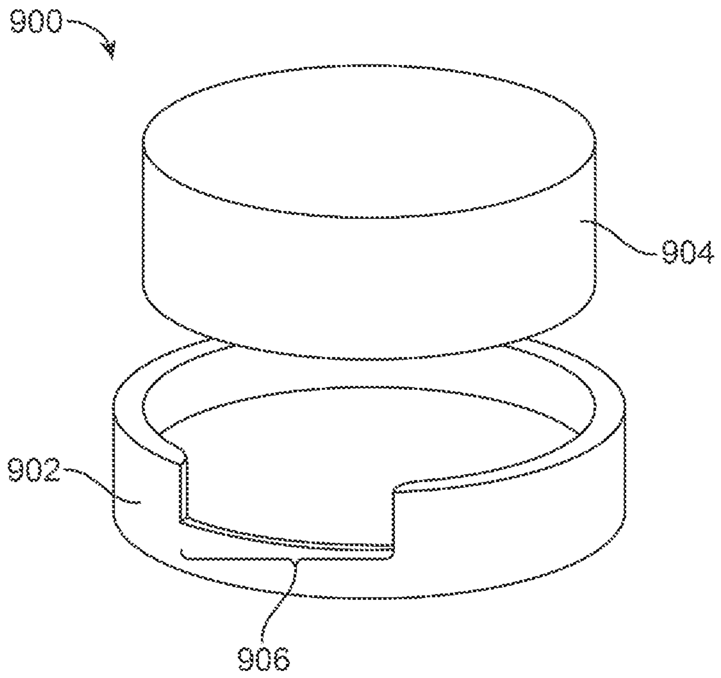
FIG. 9A illustrates a first view of a mold for manufacturing a polymer enclosure, according to an aspect of the present disclosure.

FIG. 9A illustrates a first view of a mold 900 for manufacturing a polymer enclosure with a passthrough slit, according to an aspect of the present disclosure. As described above with respect to FIG. 5, the enclosure or a portion of the enclosure may be placed in a mold for the sealing process. The piece(s) of polymer may melt and reflow within such a mold. The mold 900 depicted in FIG. 9A includes a mold base 902 and a mold top 904. The mold base 902 includes an opening 906. The insulated wires can lie in the opening 906 so that they extend out of the mold 900.

Figure 9B:
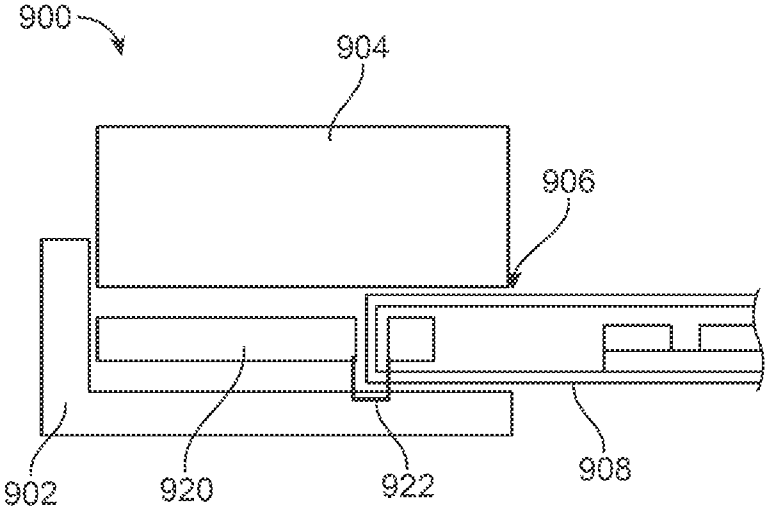
FIG. 9B illustrates a second view of a mold for manufacturing a polymer enclosure, with wires in place, according to an aspect of the present disclosure.

FIG. 9B illustrates a second view of a mold 900 for manufacturing a polymer enclosure, with wires 908 and a piece of polymer 920 in place, according to an aspect of the present disclosure. The mold 900 includes a mold top 904 and a mold base 902 with an opening 906. The piece of polymer 920 is placed in the mold 900. The wires 908 extend out of the opening 906 in the mold 900. The piece of polymer 920 has a slit corresponding to a melt zone 922 for polymer reflow.

As noted above with respect to FIG. 1, the implantable device may include various electronics within the enclosure. In some implementations, part or the entirety of the electronics could be pre-connected onto the insulated wire before the slit formation process. When the wires are fully adhered to the polymer piece in the mold, a bond pad region of the insulation material (e.g., PI) will be on the one side of the piece of polymer and the electrode region of the insulated wires will be on the opposite side. The final configuration could have the bond-pad region either within the mold or outside of the mold depending on the need. When the electronics are pre-attached, the bond-pad region can be placed outside of the mold to prevent damage to the electronics. Alternatively, the wires can be sealed to the slit before attaching electronics to the wires.

Figure 10:
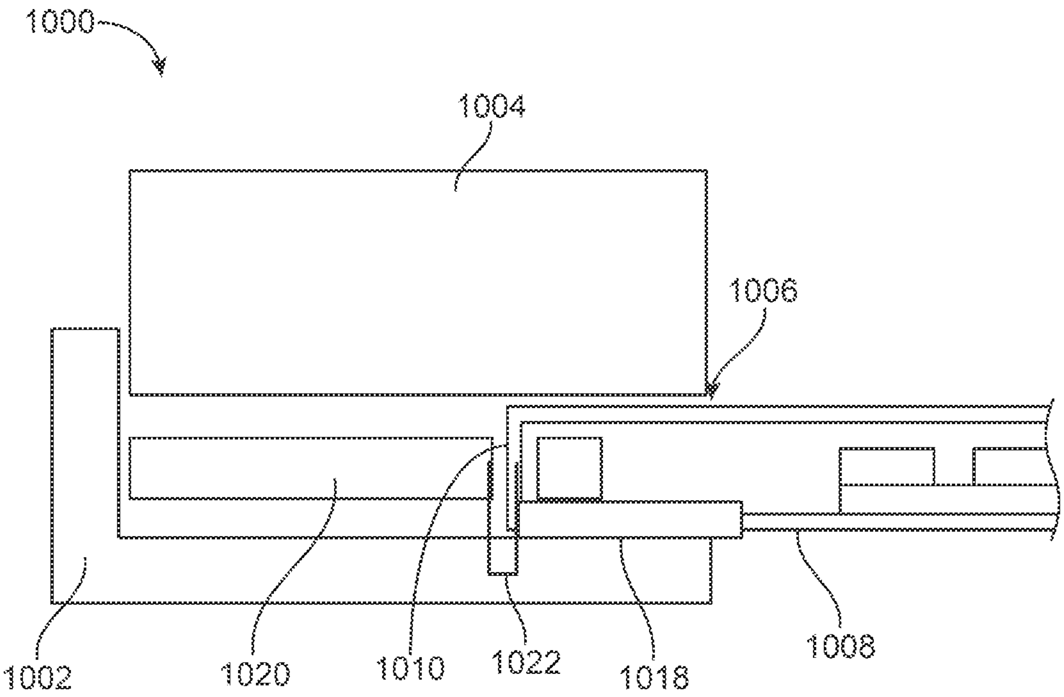
FIG. 10 illustrates a mold for manufacturing a polymer enclosure, with wires and a stiffener in place, according to another aspect of the present disclosure.

FIG. 10 illustrates a mold 1000 for manufacturing a polymer enclosure, with wires and a stiffener in place, according to another aspect of the present disclosure. Similarly to the mold 900 depicted in FIGS. 9A and 9B, the mold 1000 includes a mold top 1004 and a mold base 1002 with an opening 1006 for wires 1008 to feed through. In a sealing process, a piece of polymer 1020 is melted to reflow and seal around each of a set of wires 1008 in a melt zone 1022. In some embodiments, a liner is attached onto the first piece of polymer to prevent certain parts of the insulated wires from sticking onto the piece of polymer.

In some embodiments, a stiffener 1018 is placed between the polymer (and potentially liner) and the mold 1000. The stiffener 1018 can be used to temporarily support the wires 1008 during the sealing process. The stiffener 1018 can be used to protect the wires 1008 from damage during the sealing process. The stiffener 1018 may also server to maintain alignment of the insulated wire 1008. In some implementations, the stiffener 1018 is composed of polyimide film such as poly (4,4'-oxydiphenylene-pyromellitimide), also known as Kapton. The stiffener 1018 can be removed after sealing. In some implementations, the stiffener is applied to a portion of the length of the wires including where the wires overlap the mold 1000, as shown in FIG. 10.

Slit Fabrication Flow

Figure 11:
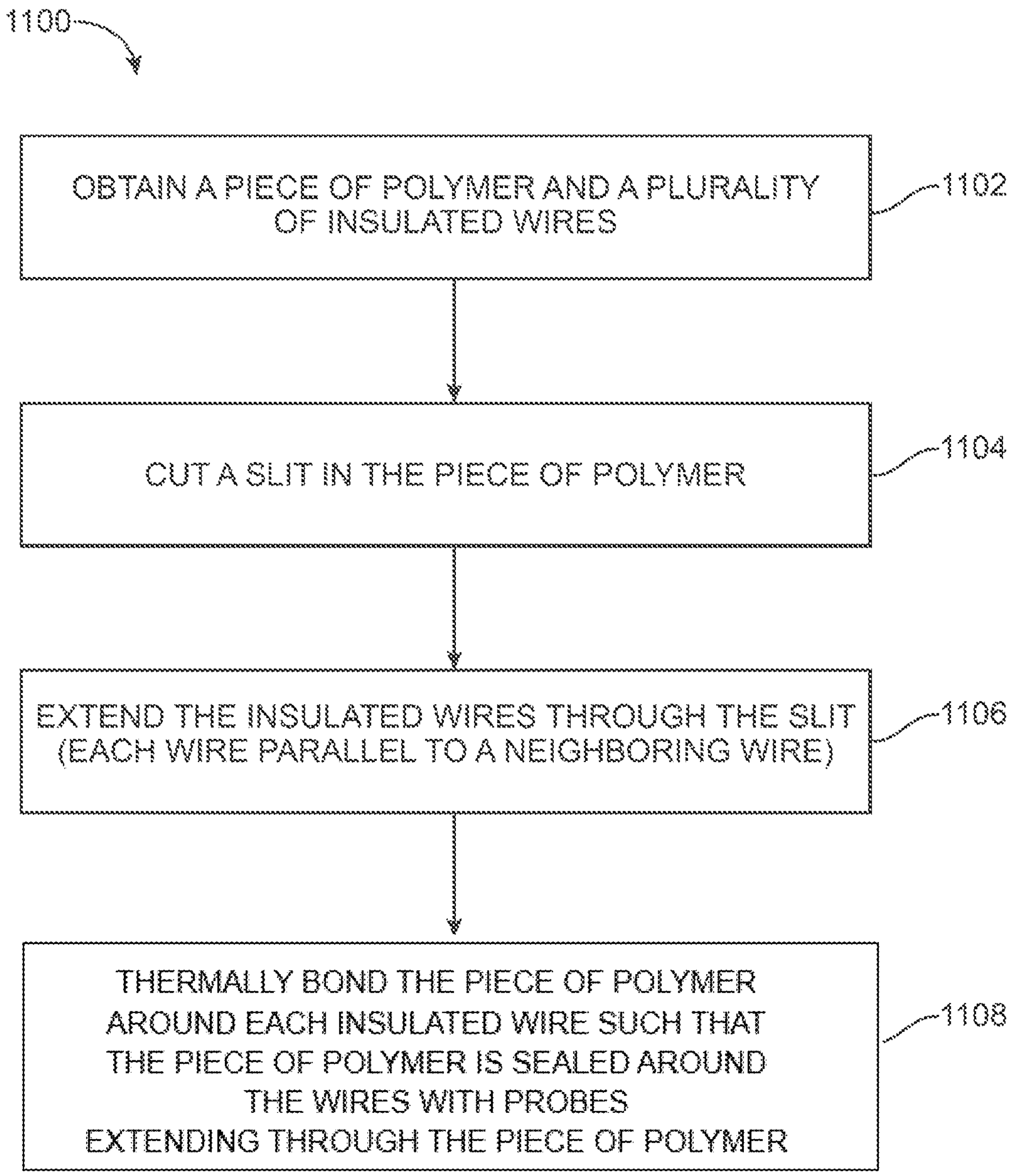
FIG. 11 is an example flowchart describing a method of manufacturing an enclosure with a passthrough slit, according to aspects of the present disclosure.

FIG. 11 is a flowchart illustrating a method 1100 of manufacturing an enclosure with a passthrough slit, with various steps, or portions thereof, represented in the disclosed flowchart blocks.

At block 1102, the method can begin with obtaining a piece of polymer and a plurality of insulated wires. As described above with respect to FIG. 1, the piece of polymer may be a piece of polymeric material with one or more flat surfaces. In some embodiments, the piece of polymer is composed of PCTFE. As described above with respect to FIG. 1, the plurality of insulated wires may include hundreds or thousands of wires insulated with a thin film made of material such as PI. The wires may be attached to each other at one or more ends, and along the length of the wires, be closely spaced from each other by a distance on the order of μm.

At block 1104, the method includes cutting a slit in the piece of polymer. The slit may be across an entire diameter of the piece of polymer, cutting the piece of polymer into two pieces. Alternatively, the slit may be a partial cut that does not extend to the edges of the piece of polymer. The slit should be long enough to allow passage of the plurality of wires. The slit should also be smooth, for ease of passthrough of the wires and to avoid damage to the wires. In some implementations, the slit may be widened with forceps and/or sanded down to provide appropriate clearance for the insulated wires.

At block 1106, the method includes extending a plurality of insulated wires through the slit. The wires are placed through the slit so that each wire is parallel to a neighboring wire. The wires are passed through the slit, so that a portion of the wires are on one side of the slit and another portion of the wires extend through the other side of the slit, as illustrated in FIG. 4.

In some implementations, the piece of polymer and the insulated wires are placed into a mold. The polymer may be disposed in a lower portion of the mold, and an upper portion of the mold is placed on top, as illustrated in FIGS. 5-6 and 9A-10. As shown in FIG. 9B, the mold can include an opening. The wires can be arranged to extend flatly through the opening in the mold. A stiffener may further be disposed onto the plurality of insulated wires. For example, the stiffener is placed under the wires along a portion of the wires to protect the wires during the sealing process, as illustrated in FIG. 10.

At block 1108, the piece of polymer is thermally bonded around each wire. The piece of polymer is thermally bonded so that the piece of polymer is sealed around insulation of each wire, with a portion of each wire extending through the piece of polymer.

In some embodiments, the piece of polymer is thermally bonded around each wire using thermocompression. Pressure is applied to the piece of polymer and the plurality of insulated wires. The piece of polymer may be placed into the mold and clamped to exert pressure on the piece of polymer. For example, a C-clamp can be applied, as shown in FIG. 7, to mechanically squeeze the polymer. Alternatively, other means of applying pressure can be used, such as a piston or hydraulic press. In some implementations, the polymer and wires are positioned so that the wires are squeezed within the slit.

The piece of polymer and the plurality of insulated wires are heated. The heating may be performed using a furnace, as shown in FIG. 8. Alternatively, other heating means may be used, such as a hot plate. The temperature applied should be high enough to melt the polymer piece without damaging the wires. In some implementations, the piece of polymer and the insulated wires are heated to a temperature between 250 degrees Celsius (C) and 350 degrees Celsius (C). This temperature range is appropriate, for example, when the piece of polymer is composed of PCTFE, which melts at around 200-215 degrees C., and the insulation of the wires is composed of PI, which decomposes at around 400 degrees C. The mass flow properties of PCTFE allow it to reflow and fuse with itself at temperature above its melting point. The sealing steps allow the PCTFE piece of polymer to fuse around the insulated wires following a thermocompression bonding.

The temperature, pressure, time of thermocompression, and environment of thermocompression may all contribute to how the polymer flows within the mold. These factors can be controlled so that the appropriate amount of polymer flow occurs. In some embodiments, the thermal bonding is performed for between 10 minutes and 15 minutes. In some implementations, the thermal bonding is performed in a pure nitrogen environment. The higher the pressure, temperature, and time, the more the PCTFE will melt and flow. The temperatures, pressures, and times noted above have been found to produce an appropriate amount of reflow without damaging other components, cracking the polymer, or causing too much polymer flow. Too much polymer flow, can, for example, alter the overall profile of the enclosure shape and size.

Once the slit is sealed around the wires, the piece of polymer is substantially hermetically sealed around the wires. After the completion of the reflow step, the piece of polymer with passthrough slit and wires sealed thereto may be released from the mold. The heater and clamping devices may be deactivated after the polymer has melted and adhered around the insulation of the insulated wires.

In some embodiments, the first piece of polymer, with the wires extending through the sealed slit, is joined to a second piece of polymer to form an enclosure for an implantable device. As illustrated in FIG. 1, the piece of polymer with the wires through the slit can be used as a first portion of the enclosure. The piece of polymer (e.g., a first piece of polymer) can be thermally sealed to a second piece of polymer. In some implementations, before sealing the two pieces of polymer together, active electronics are disposed within the two pieces of polymer. The sealing process for sealing the two pieces of polymer may be similar to the process described above for sealing the slit. Thermocompression molding at greater 200 degrees C. can be performed to seal the two pieces of polymer together. Due to the presence of active electronics or other sensitive components, this second sealing process may be performed at a lower temperature, lower pressure, and/or shorter time than the process of sealing the slit. For example, the two pieces of polymer are sealed together at a maximum temperature of between 255 degrees C. and 260 degrees C.

After the polymer portions are melted and adhered, the implantable device may be cooled. For example, after a predetermined time of applying heat and pressure to the PCTFE portions, the sealing system transitions to a cooling mode. The sealing system may monitor the temperature until the implantable device is cooled enough for unloading. The sealing system may notify a user (e.g., with an alarm sound) once cooling is complete. The user can then detach the implantable device from the sealing system (e.g., by unscrewing any screws, unclamping any clamps, etc.).

In some embodiments, some or all of the sealing process is performed automatically. A controller may monitor and adjust temperature and pressure applied for the reflow and sealing process. The controller may be instructed using instructions stored on a computer system as described with respect to FIG. 12.

Example Computer System

Figure 12:
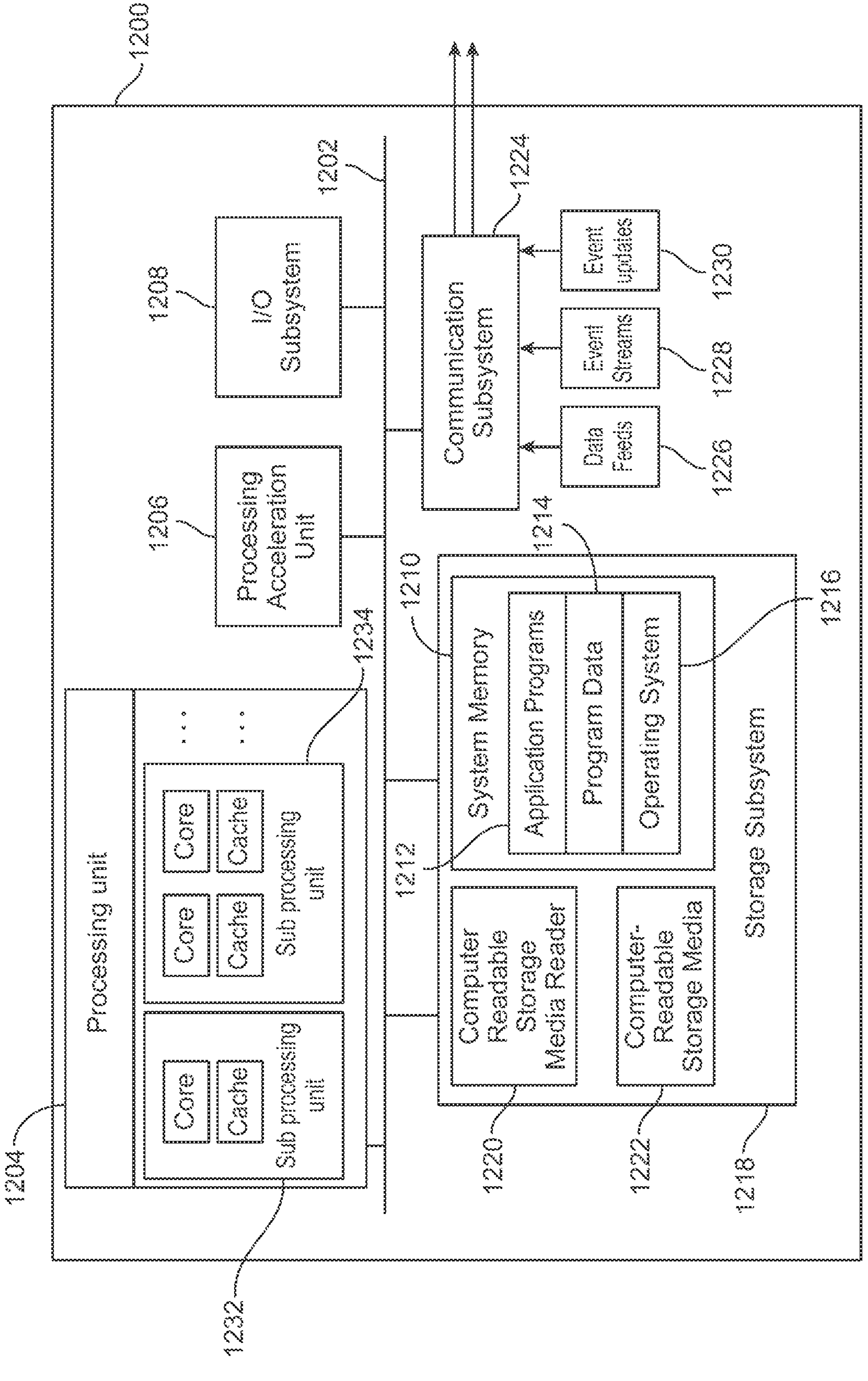
FIG. 12 illustrates an example computer system that may be used to implement certain embodiments.

FIG. 12 illustrates an example computer system 1200 that may be used to implement certain embodiments. For example, in some embodiments, computer system 1200 may be used to implement any of the systems for manufacturing components of an implantable device described above. As shown in FIG. 12, computer system 1200 includes various subsystems including a processing subsystem 1204 that communicates with a number of other subsystems via a bus subsystem 1202. These other subsystems may include a processing acceleration unit 1206, an I/O subsystem 1208, a storage subsystem 1218, and a communications subsystem 1224. Storage subsystem 1218 may include non-transitory computer-readable storage media including storage media 1222 and a system memory 1210.

Bus subsystem 1202 provides a mechanism for letting the various components and subsystems of computer system 1200 communicate with each other as intended. Although bus subsystem 1202 is shown schematically as a single bus, alternative embodiments of the bus subsystem may utilize multiple buses. Bus subsystem 1202 may be any of several types of bus structures including a memory bus or memory controller, a peripheral bus, a local bus using any of a variety of bus architectures, and the like. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard, and the like.

Processing subsystem 1204 controls the operation of computer system 1200 and may comprise one or more processors, application specific integrated circuits (ASICs), or field programmable gate arrays (FPGAs). The processors may include be single core or multicore processors. The processing resources of computer system 1200 can be organized into one or more processing units 1232, 1234, etc. A processing unit may include one or more processors, one or more cores from the same or different processors, a combination of cores and processors, or other combinations of cores and processors. In some embodiments, processing subsystem 1204 can include one or more special purpose co-processors such as graphics processors, digital signal processors (DSPs), or the like. In some embodiments, some or all of the processing units of processing subsystem 1204 can be implemented using customized circuits, such as application specific integrated circuits (ASICs), or field programmable gate arrays (FPGAs).

In some embodiments, the processing units in processing subsystem 1204 can execute instructions stored in system memory 1210 or on computer readable storage media 1222. In various embodiments, the processing units can execute a variety of programs or code instructions and can maintain multiple concurrently executing programs or processes. At any given time, some or all of the program code to be executed can be resident in system memory 1210 and/or on computer-readable storage media 1222 including potentially on one or more storage devices. Through suitable programming, processing subsystem 1204 can provide various functionalities described above. In instances where computer system 1200 is executing one or more virtual machines, one or more processing units may be allocated to each virtual machine.

In certain embodiments, a processing acceleration unit 1206 may optionally be provided for performing customized processing or for off-loading some of the processing performed by processing subsystem 1204 so as to accelerate the overall processing performed by computer system 1200.

I/O subsystem 1208 may include devices and mechanisms for inputting information to computer system 1200 and/or for outputting information from or via computer system 1200. In general, use of the term input device is intended to include all possible types of devices and mechanisms for inputting information to computer system 1200. User interface input devices may include, for example, a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may also include motion sensing and/or gesture recognition devices such as the Microsoft Kinect® motion sensor that enables users to control and interact with an input device, the Microsoft Xbox® 360 game controller, devices that provide an interface for receiving input using gestures and spoken commands. User interface input devices may also include eye gesture recognition devices such as the Google Glass® blink detector that detects eye activity (e.g., “blinking” while taking pictures and/or making a menu selection) from users and transforms the eye gestures as inputs to an input device (e.g., Google Glass®). Additionally, user interface input devices may include voice recognition sensing devices that enable users to interact with voice recognition systems (e.g., Siri® navigator) through voice commands.

Other examples of user interface input devices include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, and medical ultrasonography devices. User interface input devices may also include, for example, audio input devices such as MIDI keyboards, digital musical instruments and the like.

In general, use of the term output device is intended to include all possible types of devices and mechanisms for outputting information from computer system 1200 to a user or other computer. User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. For example, user interface output devices may include, without limitation, a variety of display devices that visually convey text, graphics and audio/video information such as monitors, printers, speakers, headphones, automotive navigation systems, plotters, voice output devices, and modems.

Storage subsystem 1218 provides a repository or data store for storing information and data that is used by computer system 1200. Storage subsystem 1218 provides a tangible non-transitory computer-readable storage medium for storing the basic programming and data constructs that provide the functionality of some embodiments. Storage subsystem 1218 may store software (e.g., programs, code modules, instructions) that when executed by processing subsystem 1204 provides the functionality described above. The software may be executed by one or more processing units of processing subsystem 1204. Storage subsystem 1218 may also provide a repository for storing data used in accordance with the teachings of this disclosure.

Storage subsystem 1218 may include one or more non-transitory memory devices, including volatile and non-volatile memory devices. As shown in FIG. 12, storage subsystem 1218 includes a system memory 1210 and a computer-readable storage media 1222. System memory 1210 may include a number of memories including a volatile main random access memory (RAM) for storage of instructions and data during program execution and a non-volatile read only memory (ROM) or flash memory in which fixed instructions are stored. In some implementations, a basic input/output system (BIOS), containing the basic routines that help to transfer information between elements within computer system 1200, such as during start-up, may typically be stored in the ROM. The RAM typically contains data and/or program modules that are presently being operated and executed by processing subsystem 1204. In some implementations, system memory 1210 may include multiple different types of memory, such as static random access memory (SRAM), dynamic random access memory (DRAM), and the like.

By way of example, and not limitation, as depicted in FIG. 12, system memory 1210 may load application programs 1212 that are being executed, which may include various applications such as Web browsers, mid-tier applications, relational database management systems (RDBMS), etc., program data 1214, and an operating system 1216. By way of example, operating system 1216 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, Palm® OS operating systems, and others.

Computer-readable storage media 1222 may store programming and data constructs that provide the functionality of some embodiments. Computer-readable media 1222 may provide storage of computer-readable instructions, data structures, program modules, and other data for computer system 1200. Software (programs, code modules, instructions) that, when executed by processing subsystem 1204 provides the functionality described above, may be stored in storage subsystem 1218. By way of example, computer-readable storage media 1222 may include non-volatile memory such as a hard disk drive, a magnetic disk drive, an optical disk drive such as a CD ROM, DVD, a Blu-Ray® disk, or other optical media. Computer-readable storage media 1222 may include, but is not limited to, Zip® drives, flash memory cards, universal serial bus (USB) flash drives, secure digital (SD) cards, DVD disks, digital video tape, and the like. Computer-readable storage media 1222 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs.

In certain embodiments, storage subsystem 1218 may also include a computer-readable storage media reader 1220 that can further be connected to computer-readable storage media 1222. Reader 1220 may receive and be configured to read data from a memory device such as a disk, a flash drive, etc.

In certain embodiments, computer system 1200 may support virtualization technologies, including but not limited to virtualization of processing and memory resources. For example, computer system 1200 may provide support for executing one or more virtual machines. In certain embodiments, computer system 1200 may execute a program such as a hypervisor that facilitated the configuring and managing of the virtual machines. Each virtual machine may be allocated memory, compute (e.g., processors, cores), I/O, and networking resources. Each virtual machine generally runs independently of the other virtual machines. A virtual machine typically runs its own operating system, which may be the same as or different from the operating systems executed by other virtual machines executed by computer system 1200. Accordingly, multiple operating systems may potentially be run concurrently by computer system 1200.

Communications subsystem 1224 provides an interface to other computer systems and networks. Communications subsystem 1224 serves as an interface for receiving data from and transmitting data to other systems from computer system 1200. For example, communications subsystem 1224 may enable computer system 1200 to establish a communication channel to one or more client devices via the Internet for receiving and sending information from and to the client devices. For example, the communication subsystem may be used to receive speech input from a client device and send a value to the client device in response.

Communication subsystem 1224 may support both wired and/or wireless communication protocols. For example, in certain embodiments, communications subsystem 1224 may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.XX family standards, or other mobile communication technologies, or any combination thereof), global positioning system (GPS) receiver components, and/or other components. In some embodiments communications subsystem 1224 can provide wired network connectivity (e.g., Ethernet) in addition to or instead of a wireless interface.

Communication subsystem 1224 can receive and transmit data in various forms. For example, in some embodiments, in addition to other forms, communications subsystem 1224 may receive input communications in the form of structured and/or unstructured data feeds 1226, event streams 1228, event updates 1230, and the like. For example, communications subsystem 1224 may be configured to receive (or send) data feeds 1226 in real-time from users of social media networks and/or other communication services such as Twitter® feeds, Facebook® updates, web feeds such as Rich Site Summary (RSS) feeds, and/or real-time updates from one or more third party information sources.

In certain embodiments, communications subsystem 1224 may be configured to receive data in the form of continuous data streams, which may include event streams 1228 of real-time events and/or event updates 1230, that may be continuous or unbounded in nature with no explicit end. Examples of applications that generate continuous data may include, for example, sensor data applications, financial tickers, network performance measuring tools (e.g. network monitoring and traffic management applications), clickstream analysis tools, automobile traffic monitoring, and the like.

Communications subsystem 1224 may also be configured to communicate data from computer system 1200 to other computer systems or networks. The data may be communicated in various different forms such as structured and/or unstructured data feeds 1226, event streams 1228, event updates 1230, and the like to one or more databases that may be in communication with one or more streaming data source computers coupled to computer system 1200.

Computer system 1200 can be one of various types, including a handheld portable device (e.g., an iPhone® cellular phone, an iPad® computing tablet, a PDA), a wearable device (e.g., a Google Glass® head mounted display), a personal computer, a workstation, a mainframe, a kiosk, a server rack, or any other data processing system. Due to the ever-changing nature of computers and networks, the description of computer system 1200 depicted in FIG. 12 is intended only as a specific example. Many other configurations having more or fewer components than the system depicted in FIG. 12 are possible. Based on the disclosure and teachings provided herein, a person of ordinary skill in the art will appreciate other ways and/or methods to implement the various embodiments.

It should be appreciated that the robotic system handling, coupling with, and engaging with one or more portions of a probe device can include a control system (or microprocessor controller) having one or more microprocessors/processing devices that can further be a component of the overall system. The control system can be local or remote to the robotic system, and can also include a display interface and/or operational controls configured to be handled by a user to alter the program of the robotic arm, to visualize the probe device, to visualize biological tissue into which the probe device is being inserted, and change configurations of the robotic device, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A method for manufacturing an implantable device, the method comprising:

cutting a slit in a piece of polymer;

extending a plurality of insulated wires through the slit, each wire of the insulated wires being parallel to a neighboring wire of the insulated wires; and thermally bonding the piece of polymer around each wire of the plurality of insulated wires such that the piece of polymer is sealed around insulation of each wire with a portion of each wire of the plurality of insulated wires extending through the piece of polymer, wherein the polymer comprises polychlorotrifluoroethylene (PCTFE).

2. The method of claim 1, wherein:

insulation of the insulated wires is composed of polyimide.

3. The method of claim 1, further comprising, before the thermally bonding:

placing the piece of polymer, with the plurality of insulated wires disposed through the slit, into a mold.

4. The method of claim 3, wherein the thermally bonding comprises:

applying pressure to the piece of polymer and the plurality of insulated wires in the mold;

and heating the piece of polymer and the plurality of insulated wires.

5. The method of claim 4, wherein:

the piece of polymer and the insulated wires are heated to a temperature between 250 degrees Celsius (C) and 350 degrees Celsius (C).

6. The method of claim 1, wherein:

the thermally bonding is performed for between 10 minutes and 15 minutes.

7. The method of claim 1, wherein:

the thermally bonding is performed in a pure nitrogen environment.

8. The method of claim 1, wherein:

the extending the plurality of insulated wires through the slit is performed at less than 100 degrees Celsius (C).

9. The method of claim 1, further comprising, before the thermally bonding:

placing the piece of polymer, with the plurality of insulated wires disposed through the slit, into a mold, wherein the mold comprises an opening; and when the piece of polymer, with the plurality of insulated wires disposed through the slit, is placed in the mold, a plurality of probes extend flatly through the opening in the mold.

10. The method of claim 1, further comprising, before the thermally bonding: disposing a stiffener onto the plurality of insulated wires.

11. The method of claim 10, wherein:

the stiffener is composed of poly (4,4'-oxydiphenylene-pyromellitimide).

12. The method of claim 1, wherein the piece of polymer is a first piece of polymer, the method further comprising:

obtaining a second piece of polymer; and after the thermally bonding, thermally sealing the first piece of polymer to the second piece of polymer.

13. A method for manufacturing an implantable device, the method comprising:

cutting a slit in a piece of polymer;

extending a plurality of insulated wires through the slit, each wire of the insulated wires being parallel to a neighboring wire of the insulated wires; and thermally bonding the piece of polymer around each wire of the plurality of insulated wires such that the piece of polymer is sealed around insulation of each wire with a portion of each wire of the plurality of insulated wires extending through the piece of polymer, wherein the method further comprises, before the thermally bonding:

placing the piece of polymer, with the plurality of insulated wires disposed through the slit, into a mold.

14. A method for manufacturing an implantable device, the method comprising:

cutting a slit in a piece of polymer;

extending a plurality of insulated wires through the slit, each wire of the insulated wires being parallel to a neighboring wire of the insulated wires; and thermally bonding the piece of polymer around each wire of the plurality of insulated wires such that the piece of polymer is sealed around insulation of each wire with a portion of each wire of the plurality of insulated wires extending through the piece of polymer, wherein the piece of polymer is a first piece of polymer, the method further comprising:

obtaining a second piece of polymer; and after the thermally bonding, thermally sealing the first piece of polymer to the second piece of polymer.

* * * * *